United States Patent
Maignan et al.

Patent Number: 5,068,393
Date of Patent: Nov. 26, 1991

[54] AROMATIC DERIVATIVES OF BUTYRIC ACID, A PROCESS FOR THEIR PREPARATION AND THEIR USE IN COSMETICS AND IN HUMAN AND VETERINARY MEDICINE

[75] Inventors: Jean Maignan, Tremblay les Gonesse; Gérard Malle, Viliers sur Morin; Gérard Lang, Saint Gratien, all of France

[73] Assignee: Societe Anonyme Dite: L'Oreal, Paris, France

[21] Appl. No.: 181,017

[22] Filed: Apr. 4, 1988

[30] Foreign Application Priority Data

Apr. 3, 1987 [FR] France .................. 87 04711

[51] Int. Cl.$^5$ .................. C07C 69/76
[52] U.S. Cl. .................. 560/51; 562/462; 536/119; 564/180; 544/175; 544/391; 546/226; 548/530; 514/844
[58] Field of Search .................. 560/51; 562/462; 538/119; 564/180; 544/175, 391; 546/226; 548/530; 514/844

[56] References Cited

FOREIGN PATENT DOCUMENTS 1566213 5/1969 France .
2300551 9/1976 France .
610875 5/1979 Switzerland .

OTHER PUBLICATIONS

Neudeck, H. et al., Monatsh. Chem. 116(5) 661-76, 1985.
Neudeck, H. et al., Monatsh. Chem. 112(6-7) 801-23, 1981.
Tatta, K. R. et al., J. Chem. Soc. C(7) 893-900, 1968.

Primary Examiner—Paul J. Killos
Attorney, Agent, or Firm—Cushman, Darby & Cushman

[57] ABSTRACT

An aromatic deviative of butyric acid has the formula

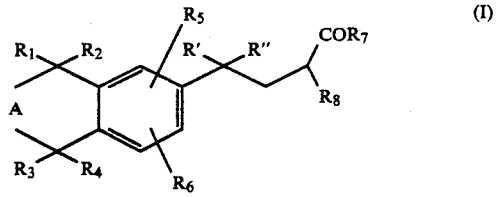

(I)

wherein $R_1$, $R_2$, $R_3$ and $R_4$, each independently, represent hydrogen or alkyl, with at least two of $R_1$-$R_4$ being other than hydrogen, A represents methylene or dimethylene; when A represents dimethylene, $R_1$ and $R_3$ can together form methylene or dimethylene, $R_5$ and $R_6$ represent hydrogen, halogen, alkyl, alkoxy or hydroxy, R' represents hydrogen, hydroxy, alkoxy or acyloxy, R" represents hydrogen or alkoxy, or R' and R" taken together form oxo or hydroxyimino, $R_8$ represents hydrogen or alkyl and $R_7$ represents —$OR_9$ or

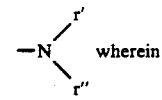 wherein $R_9$ represents hydrogen, alkyl, monohydroxyalkyl, polyhydroxyalkyl, aryl or aralkyl, optionally substituted, a sugar residue, carboxyalkyl or alkoxycarbonylalkyl, r' and r" represent hydrogen, alkyl, monohydroxyalkyl optionally interrupted by a heteroatom, polyhydroxyalkyl, aryl or benzyl optionally substituted, amino acid residue or aminated sugar residue, or r' and r" taken together form a heterocycle, optionally substituted by a $C_1$-$C_3$ hydroxyalkyl, and to the salts of the compounds of formula I, to their optical isomers as well as the tautomers of the compounds of formula I. These aromatic derivatives of butyric acid are useful in human and veterinary medicines as well as in cosmetic compositions.

21 Claims, No Drawings

AROMATIC DERIVATIVES OF BUTYRIC ACID, A PROCESS FOR THEIR PREPARATION AND THEIR USE IN COSMETICS AND IN HUMAN AND VETERINARY MEDICINE

The present invention relates to new aromatic derivatives of butyric acid, to a process for their preparation and to their use in cosmetic compositions and in human and veterinary medicine.

The compounds according to the present invention, due to their inhibiting activity on the synthesis of lipids, are of great interest in cosmetics for the treatment of the scalp and skin exhibiting an oily appearance.

These new aromatic derivatives of butyric acid according to the present invention can be represented by the following general formula

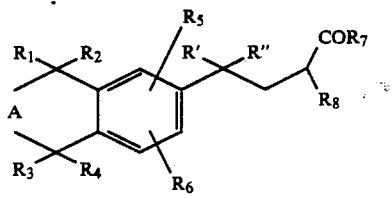

wherein
$R_1$, $R_2$, $R_3$ and $R_4$, each independently, represent hydrogen or lower alkyl, with at least two of radicals $R_1$–$R_4$ being other than hydrogen, A represents methylene or dimethylene, substituted or not by lower alkyl; when A represents dimethylene, $R_1$ and $R_3$ can form together a methylene or dimethylene radical, $R_5$ and $R_6$ represent hydrogen, halogen, lower alkyl, lower alkoxy or hydroxyl, R' represents hydrogen, hydroxyl, lower alkoxy or $C_1$–$C_4$ acyloxy, R'' represents hydrogen or lower alkoxy, or R' and R'', taken together form an oxo radical (=O) or hydroxyimino radical (=N—OH), $R_8$ represents hydrogen or lower alkyl, $R_7$ represents —$OR_9$ or ·

tuted, an amino-acid residue or aminated sugar residue or, taken together, form a heterocycle optionally substituted by a $C_1$–$C_3$ hydroxyalkyl, and
the salts of said compound of formula I and their optical isomers, as well as the tautomeric forms of the compounds of formula I (in particular the corresponding lactones and lactams).

By lower alkyl is meant an alkyl having 1–6 carbon atoms.

By lower alkyl or alkyl having up to 20 carbon atoms is meant principally methyl, ethyl, propyl, isopropyl, butyl, tert.butyl, 2-ethylhexyl, octyl, dodecyl, hexadecyl and octadecyl.

By monohydroxyalkyl is meant a radical having 2–6 carbon atoms and principally 2-hydroxyethyl, 2-hydroxypropyl or 2-hydroxyethoxyethyl.

By polyhydroxyalkyl is meant a radical containing 3–6 carbon atoms and 2–5 hydroxyl groups, such as 2,3-dihydroxy propyl, 1,3-dihydroxy propyl or the residue of pentaerythritol.

Representative lower alkoxy radicals include methoxy, isopropoxy, butoxy and tert.butoxy.

By a sugar residue is meant a residue derived from glucose, mannose, erythrose or galactose.

Representative aminated sugar residues inlcude those derived from glucosamine, galactosamine, mannosamine or meglumine.

When r' and r'', taken together, form with the nitrogen atom to which they are attached a heterocycle, the heterocycle is preferably piperidino, piperazino, morpholino, pyrrolidino or 4-(2-hydroxyethyl) piperazino.

When the compounds of the present invention are provided in the form of salts, it is a question either of zinc salts, alkali or akaline earth metal salts or salts of an organic amine when they include at least one free acid function, or salts of a mineral or organic acid, principally the hydrochloride, hydrobromide or citrate when they include at least one amine function.

The compounds of the present invention can be provided in their tautomeric form when R' and R'', taken together, form an oxo radical and $R_7$ represents

at least one of the substituents r' and r'' being hydrogen, these compounds then being lactams which can be represented by formula III

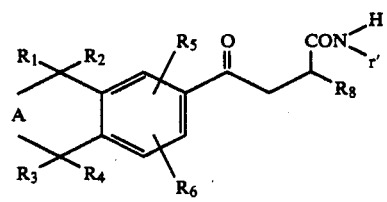

(II)

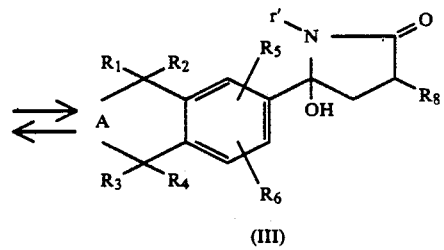

(III)

$R_9$ represents hydrogen or alkyl having 1–20 carbon atoms, monohydroxyalkyl, polyhydroxyalkyl, aryl or aralkyl, optionally substituted, a sugar residue, carboxyalkyl or alkoxycarbonylalkyl, r' and r'' represent hydrogen, lower alkyl, monohydroxyalkyl optionally interrupted by a heteroatom, polyhydroxyalkyl, aryl or benzyl optionally substi- Particularly preferred compounds of formula I, according to the invention, include those having the following general formula:

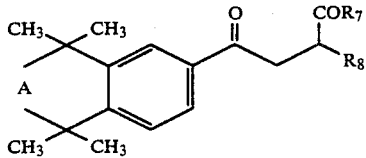

wherein

A represents —(CH₂)₂— or

R₇ represents —OR₉ or

R₉ represents hydrogen or lower alkyl, r' represents hydrogen and r" represents alkyl having 1-8 carbon atoms, monohydroxyalkyl optionally interrupted by a heteroatom, or polyhydroxy alkyl or r' and r", taken together, form with the nitrogen atom to which they are attached 4-(2-hydroxyethyl) piperazinyl, and R₈ represents hydrogen or methyl.

Representative compounds of formula I include the following:

4-(5,5,8,8-tetramethyl-5,6,7,8-tetrahydro-2-naphthyl)-4-oxo-2-methyl butyric acid,
4-(5,8-methano-5,6,7,8-tetrahydro-2-naphthyl)-4-oxo-2-methyl butyric acid,
4-(1,1,2,3,3,-pentamethyl-5-indanyl)-4-oxo-2-methyl butyric acid,
4-(1,1,3,3-tetramethyl-5-indanyl)-4-oxo-2-methyl butyric acid,
4-(5,5,8,8-tetramethyl-5,6,7,8-tetrahydro-2-naphthyl)-4-oxo butyric acid,
4-(5,8-methano-5,6,7,8-tetrahydro-2-naphthyl)-4-oxo butyric acid,
4-(1,1,2,3,3-pentamethyl-5-indanyl)-4-oxo butyric acid,
4-(1,1,3,3-tetramethyl-5-indanyl)-4-oxo butyric acid,
4-(1,4-dimethoxy-5,8,-methano-5,6,7,8-tetrahydro-2-naphthyl)-4-oxo-2-methyl butyric acid,
4-(1,4-dimethoxy-5,8-methano-5,6,7,8-tetrahydro-2-naphthyl)-4-oxo butyric acid,
ethyl 4-(1,1,2,3,3-pentamethyl-5-indanyl)-4-oxo butyrate,
ethyl 4-(5,5,8,8-tetramethyl-5,6,7,8-tetrahydro-2-naphthyl)-4-oxo butyrate,
ethyl 4-(1,4-dimethoxy-5,8-methano-5,6,7,8-tetrahydro-2-naphthyl)-4-oxo butyrate,
2'-ethylhexyl 4-(5,5,8,8-tetramethyl-5,6,7,8-tetrahydro-2-naphthyl)-4-oxo butyrate,
N-ethyl 4-(5,5,8,8-tetramethyl-5,6,7,8-tetrahydro-2-naphthyl)-4-oxo-2-methyl butyramide,
N-ethyl 4-(5,5,8,8-tetramethyl-5,6,7,8-tetrahydro-2-naphthyl)-4-oxo butyramide,
N-ethyl 4-(1,4-dimethoxy-5,8-methano-5,6,7,8-tetrahydro-2-naphthyl)-4-oxo butyramide,
4'-N-(2-hydroxyethyl)piperazinyl 4-(5,5,8,8-tetramethyl-5,6,7,8-tetrahydro-2-naphthyl)-4-oxo butyramide,
N-(2-hydroxyethoxyethyl) 4-(5,5,8,8-tetramethyl-5,6,7,8-tetrahydro-2-naphthyl)-4-oxo butyramide,
N-(2-hydroxyethoxyethyl) 4-(1,1,2,3,3-pentamethyl-5-indanyl)-4-oxo butyramide,
4-(5,5,8,8-tetramethyl-5,6,7,8-tetrahydro-2-naphthyl)-4-hydroxy butyric acid,
4-(1,1,2,3,3-pentamethyl-5-indanyl)-4-hydroxy butyric acid,
4-(1,4-dimethoxy-5,8-methano-5,6,7,8-tetrahydro-2-naphthyl)-4-hydroxy butyric acid,
ethyl 4-(5,5,8,8-tetramethyl-5,6,7,8-tetrahydro-2-naphthyl)-4-hydroxy imino butyrate,
4-(5,5,8,8-tetramethyl-5,6,7,8-tetrahydro-2-naphthyl)-4-hydroxy imino butyric acid,
sodium 4-(5,5,8,8-tetramethyl-5,6,7,8-tetrahydro-2-naphthyl)-4-oxo butyrate,
sodium 4-(5,5,8,8-tetramethyl-5,6,7,8-tetrahydro-2-naphthyl)-4-oxo-2-methyl butyrate,
zinc 4-(5,5,8,8-tetramethyl-5,6,7,8-tetrahydro-2-naphthyl)-4-oxo butyrate,
zinc 4-(1,4-dimethoxy-5,8-methano-5,6,7,8-tetrahydro-2-naphthyl)-4-oxo butyrate,
zinc 4-(1,1,2,3,3-pentamethyl-5-indanyl)oxo butyrate,
4-(5,5,8,8-tetramethyl-5,6,7,8-tetrahydro-2-naphthyl)-butyric acid and
zinc 4-(5,5,8,8-tetramethyl-5,6,7,8-tetrahydro-2-naphthyl)-4-oxo-2-methyl butyrate.

The present invention also relates to a process for the preparation of the compounds of formula I.

These compounds can be prepared in accordance with the following reaction scheme:

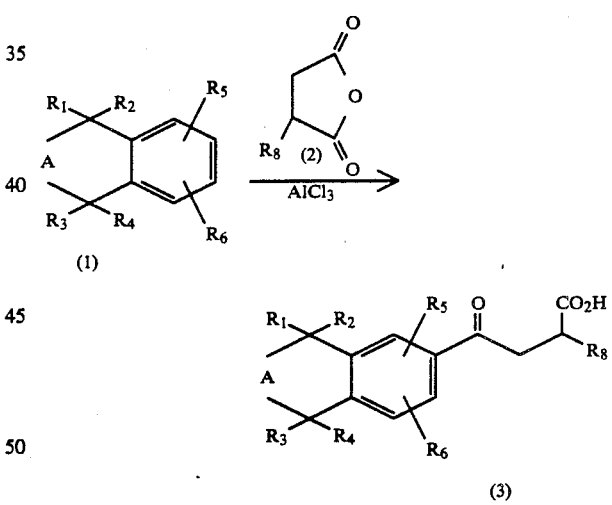

This process comprises a condensation reaction, effected under Friedel Crafts reaction conditions, of an anhydride having structure (2) on a bicyclic aromatic compound of formula (1).

This condensation reaction is carried out in the presence of a Lewis acid, such as aluminum chloride or tin chloride in a chlorinated solvent such as 1,2-dichloroethane or dichloromethane.

Representative bicyclic aromatic starting compounds of formula (1) include 1,1,4,4-tetramethyl-1,2,3,4-tetrahydro naphthalene (described in J.A.C.S. 62, 36-44, (1940), 1,4-methano-1,2,3,4-tetrahydro naphthalene or benzonorbornene (described in J.O.C., 32, 893-901, 1967), 5,8-dihydro-1,4-methano-1,2,3,4-tetrahydro naphthalene (commercial product), 1,1,3,3-tetramethyl indane and 1,1,2,3,3-pentamethyl indane (described in French patent No. 1.392.804).

Starting with the keto-acid of formula (3), there can be produced, in accordance with the present invention other forms of the compounds of the present invention.

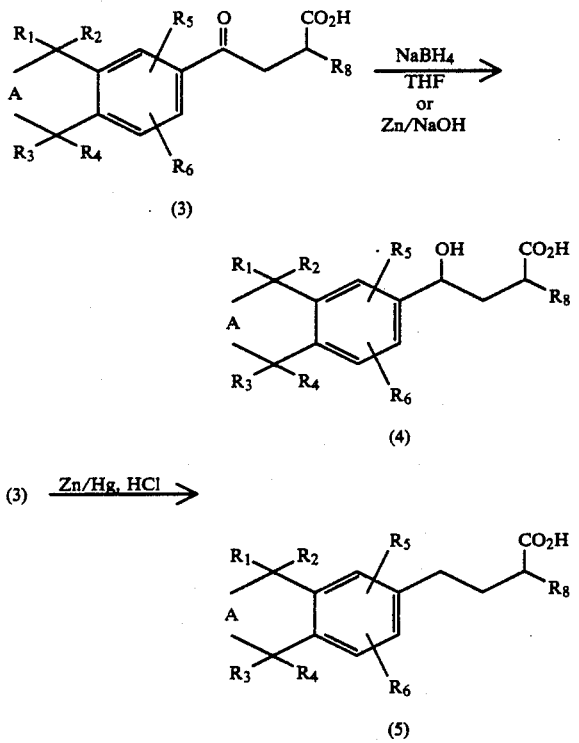

Thus, on reduction using sodium borohydride, in a solvent such as tetrahydrofuran or even by zinc in an alkaline medium, secondary alcohols of formula (4) can be produced.

Carrying out a Clemmensen reduction, using zinc amalgam in the presence of HCl, compounds of formula (5) can be produced.

The acyloxy derivatives of the compounds of formula I, (R'=acyloxy and R''=H), are obtained by reacting an activated form of an acid, such as an anhydride or acid chloride, with a compound of the present invention in which R'=OH and R''=H.

The alkoxy derivatives of the compound of formula I, (R'=alkoxy and R''=H) are also obtained starting with compounds of formula I, (R'=OH and R''=H) in accordance with known methods.

The compounds of formula I, wherein R' and R'' together form a hydroxyimino radical, are obtained by the reaction of hydroxylamine hydrochloride with corresponding carbonyl compounds in an organic solvent such as ethanol, in the presence of a mineral base, such as sodium bicarbonate, or an organic base such as triethylamine.

The compounds of formula I, in the form of esters, amides or salts, are prepared following conventional esterification, amidification or salification methods.

The compounds of formula I, in accordance with the present invention, exhibit excellent activity in the test described by J. Girard and A. Barbier, Int. Journal of Cosmetic Science, 2, 315-329 (1980) and M. Gauci and J. Oustrin, Int. Journal of Cosmetic Science 3, 227-232 (1982). These authors have, in effect, shown that the "in vitro" test of incorporating labeled glucose can be retained as an orientation test for nonhormonal antiseborrheics since this test accounts for the inhibiting activity of the synthesis of lipids.

Moreover, it is known that an increase in the secretion of sebum produces dermatologic conditions such as seborrhea, pellicules, oily skin, oily hair, whiteheads and blackheads.

These chronic phenomena of pilo-sebaceous disorders concern especially the face, chest and back.

Moreover, the acids of formula I, in accordance with the invention, wherein $R_7$=OH, exhibit good activity on "Rhino mouse", this test generally being regarded as one of the screening elements in identifying a product as having anti-acne activity.

The compounds according to the present invention are then quite particularly suitable for the treatment of excessive secretions of sebum and, principally, for the treatment of oily skin and hair, acne vulgaris, acne with comedons or polymorphous acne, senile acne, solar acne and medication induced or occupational acne.

The compounds of formula I, in accordance with the present invention, are then usefully employed in the cosmetic field, in particular for hair and body hygiene and, principally, for the treatment of skin having acne tendencies, for promoting hair growth, for combatting hair fall out, and for combatting against the oily appearance of the hair and skin.

The present invention thus relates to a cosmetic composition comprising, in a cosmetically acceptable vehicle, at least one compound of formula I, or one of its salts, or one of its isomers, this composition being provided principally in the form of a lotion, gel, soap or shampoo.

The concentration of the compounds of formula I, in the cosmetic compositions, ranges between 0.005 and 5 weight percent and preferably between 0.01 and 1 weight percent, based on the total weight of the composition.

The present invention also relates to a medicinal composition, intended principally for the treatment of various forms of acne, characterized by the fact that it contains, in a pharmaceutically acceptable vehicle at least one compound of formula I and/or one of its isomers and/or one of its salts.

As the vehicle for these compositions, any conventional vehicle can be employed, the active compound being found either in the dissolved state or in the dispersed state in the said vehicle.

The composition can be administered enterally, parenterally or topically.

When administered enterally, the medicine can be provided in the form of tablets, gelules, lozenges, syrups, suspensions, solutions, powders, granules or emulsions.

When administered parenterally, the composition can be provided in the form of solutions or suspensions, for perfusions or for injections.

The compounds according to the present invention are generally administered to a person at a daily dosage of about 0.1 mg/kg to 10 mg/kg of body weight.

When administered topically, the pharmaceutical compositions, based on the compounds of the present invention, are provided in the form of salves, tinctures, creams, ointments, powders, plasters, impregnated tampons, solutions, emulsions, lotions, gels, sprays or suspensions.

These topically applicable compositions can be provided either in anhydrous form, or in aqueous form, depending on clinical indications.

When the compounds of the present invention are employed topically, good activity of these compounds is observed on a very large range of dilution; there can be employed, principally, active product concentrations ranging from 0.01 to 10 weight percent. It is quite possible, however, to employ even higher concentrations when it is necessary for a particular therapeutic use; however the preferred concentration of the active component ranges between 0.1 and 5 weight percent, based on the total weight of the composition.

The cosmetic and medicinal compositions of the present invention can contain inert additives or even cosmetically or pharmacodynamically actives and principally:

- hydrating agents such as thiamorpholinone and its derivatives, or urea,
- anti-seborrheic agents such as S-carboxymethyl cysteine, S-benzylcysteamine and their derivatives or tioxolone,
- anti-acne agents such as benzoyl peroxide,
- antibiotics such as erythromycin and its esters, neomycin, tetracyclines or 4,5-polymethylene-3-isothiazolinones,
- agents promoting the growth of hair, such as "Minoxidil" (2,4-diamino-6-piperidino-3-pyrimidine oxide) and its derivatives, Diazoxide (7-chloro-3-methyl-1,2,4-benzothiadiazine-1,1-dioxide) and Phenytoin (5,5-diphenyl-2,4-imidazoline-dione) or even oxapropanium iodide,
- steroidal and nonsteroidal anti-inflammatory agents, carotenoids and principally, $\beta$-carotene,
- anti-psoriasis agents such as anthralin and its derivatives and 5,8,11,14-eicosatetraynoic and 5,8,11-triynoic acids and their esters and amides.

The compositions of the present invention can also contain flavor improving agents, preservatives, stabilizers, humidity regulators, pH regulators, osmotic pressure modifiers, emulsifiers, UV-A and UV-B filters, anti-oxidants such as $\alpha$-tocopherol, butylhydroxy anisole or butylhydroxy toluene.

The following nonlimiting examples are given to illustrate the preparation of the active compounds of formula I according to the invention as well as compositions containing these active compounds.

EXAMPLE I

Preparation of 4-(5,5,8,8-tetramethyl-5,6,7,8-tetrahydro-2-naphthyl)-4-oxo-2-methyl butyric acid Compound of formula I wherein $A=-CH_2-_2$, $R_1=R_2=R_3=R_4=CH_3$, $R_5=R_6=H$, $R'$, $R''=oxo$, $R_7=OH$ and $R_8=CH_3$ To a solution of 37.7 g (0.2 mole) of 1,1,4,4-tetramethyl-1,2,3,4-tetrahydro naphthalene and 22.82 g (0.2 mole) of methylsuccinic anhydride in 250 cm³ of anhydrous 1,2-dichloroethane, there are added, by portions, over a period of about 1 hour, 53.3 g (0.4 mole) of anhydrous aluminum chloride in a manner to maintain the temperature lower than or equal to 30° C. After stirring for 3 hours at ambient temperature, the reaction mixture is poured into 200 cm³ of ice water. The organic phase is decanted. The aqueous phase is again extracted twice with 100 cm³ of dichloromethane. The dichloroethane and dichloromethane phases are combined, washed with water, dried on sodium sulfate and concentrated under reduced pressure. The residue is taken up in 300 cm³ of hexane, filtered, successively washed three times with 200 cm³ of toluene and then recrystallized in isopropyl ether. After drying, 20.7 g of 4-(5,5,8,8-tetramethyl-5,6,7,8-tetrahydro-2-naphthyl)-4-oxo-2-methyl butyric acid in the form of a white solid whose melting point is 165° C. are obtained.

The NMR¹H and ¹³C spectra correspond to the expected structure.

Elemental analysis: $C_{19}H_{26}O_3$

|  | C | H | O |
|---|---|---|---|
| Calculated | 75.46 | 8.67 | 15.87 |
| Found | 75.22 | 8.72 | 16.00 |

EXAMPLE II

Preparation of 4-(5,8-methano-5,6,7,8-tetrahydro-2-naphthyl)-4-oxo-2-methyl butyric acid Compound of formula I where $A=-CH_2-_2$, $R_1,R_3=-CH_2-$, $R_2=R_4=H$, $R_5=R_6=H$, $R'$, $R''=oxo$, $R_7=OH$ and $R_8=CH_3$ To a suspension of 13.33 g (0.1 mole) of anhydrous aluminum chloride in 70 cm³ of dry dichloromethane, stirred at ambient temperature, there is slowly added, over about a 30 minute period, an equimolar solution of 7.11 g (0.05 mole) of 1,4-methano-1,2,3,4-tetrahydronaphthalene and 5.7 g (0.05 mole) of methylsuccinic anhydride in 50 cm³ of dry dichloromethane. At the end of the addition, the reaction mixture is stirred for 1 additional hour at ambient temperature, and it is then poured into 100 cm³ of ice water. The organic phase is decanted and the aqueous phase is again extracted twice with 100 cm³ of dichloromethane. The dichloromethane phases are washed with water, dried on sodium sulfate and then evaporated to dryness. The resulting crude oil is crystallized by trituration in 100 cm³ of tepid hexane. After filtration, the resulting beige solid is recrystallized in 120 cm³ of a 90/10 hexane/acetone mixture, thereby yielding 5.1 g of white crystals which are taken up in 50 cm³ of isopropyl ether, filtered and again recrystallized in 80 cm³ of a 60/40 isopropyl ether/hexane mixture. After drying, 1.7 g of 4-(5,8-methano-5,6,7,8-tetrahydro-2-naphthyl)-4-oxo-2methyl butyric acid in the form of a white solid whose melting point is 148° C. are obtained.

The NMR¹H 250 MHz and ¹³C spectra conform to the expected structure.

Elemental analysis: $C_{16}H_{18}O_2$

|  | C | H | O |
|---|---|---|---|
| Calculated | 74.39 | 7.02 | 18.58 |
| Found | 74.69 | 7.20 | 18.06 |

EXAMPLE III

Preparation of
4-(5,5,8,8-tetramethyl-5,6,7,8-tetrahydro-2-naphthyl)-4-oxo butyric acid Compound of formula I wherein $A = -CH_2-_2$, $R_1 = R_2 = R_3 = R_4 = CH_3$, $R_5 = R_6 = H$, $R', R'' = $ oxo, $R_7 = OH$ and $R_8 = H$ To a suspension of 13.18 g (0.07 mole) of 1,1,4,4-tetramethyl-1,2,3,4-tetrahydro naphthalene and 7 g (0.07 mole) of succinic anhydride in 150 cm³ of anhydrous 1,2-dichloroethane, there are added, by portions, over about a 45 minute period, 18.7 g (0.14 mole) of anhydrous aluminum chloride in a manner to maintain the temperature lower than 30° C. After stirring for 3 hours, the reaction mixture is poured into 100 cm³ of ice water. The organic phase is decanted and the aqueous phase is extracted three times with 100 cm³ of dichloromethane. The dichloroethane and dichloromethane phases are combined, washed with water, dried on sodium sulfate and concentrated under reduced pressure. The resulting crude solid is recrystallized twice in acetone, yielding 15.7 g of white crystals of 4-(5,5,8,8-tetramethyl-5,6,7,8-tetrahydro-2-naphthyl)-4-oxo butyric acid whose melting point is 178° C.

The NMR$^1$H 250 MHz spectrum conforms to the expected structure.

Elemental analysis: $C_{18}H_{24}O_3$

|  | C | H | O |
|---|---|---|---|
| Calculated | 74.97 | 8.39 | 16.45 |
| Found | 74.76 | 8.51 | 16.30 |

EXAMPLE IV

Preparation of
4-(1,1,2,3,3-pentamethyl-5-indanyl)-4-oxo butyric acid

Compound of formula I wherein

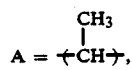

$R_1 = R_2 = R_3 = R_4 = CH_3$, $R_5 = R_6 = H$, $R', R'' = $ oxo, $R_7 = OH$ and $R_8 = H$ To a solution of 11 g of 1,1,2,3,3-pentamethyl indane (0.058 mole) and 7 g of succinic anhydride (0.07 mole) in 100 cm³ of anhydrous 1,2-dichloroethane, stirred at 0° C., there are added, by small portions, 9.4 g of aluminum chloride in a manner such that the temperature remains lower than 30° C. The reaction mixture is stirred for 3 hours at ambient temperature and then poured into 250 cm³ of ice water. The organic phase is decanted and the aqueous phase is extracted twice with 1,2-dichloroethane. The organic phases are combined, washed with water and dried on magnesium sulfate. The solvent is evaporated under reduced pressure and the resulting product is crystallized in isopropyl ether. 7 g of 4-(1,1,2,3,3-pentamethyl-5-indanyl)-4-oxo butyric acid in the form of white crystals whose melting point is 161° C. are obtained.

Elemental analysis: $C_{18}H_{24}O_3$

|  | C | H | O |
|---|---|---|---|
| Calculated | 74.97 | 8.39 | 16.64 |
| Found | 74.92 | 8.50 | 16.49 |

EXAMPLE V

Preparation of
4-(5,8-methano-5,6,7,8-tetrahydro-2-naphthyl)-4-oxo butyric acid

Compound of formula I wherein $A = -CH_2-_2$, $R_1, R_3 = -CH_2-$, $R_2 = R_4 = H$, $R_5 = R_6 = H$, $R', R'' = $ oxo, $R_7 = OH$ and $R_8 = H$, To a solution, stirred at 0° C., of 30 g of 1,4-methano-1,2,3,4-tetrahydro naphthalene (0.2 mole) and 21 g of sucinic anhydride (0.21 mole) in 300 cm³ of dichloromethane, there are added, by small portions and over about a 2 hour period, 56 g of aluminum chloride. Stirring is then maintained for 2 hours at ambient temperature. The reaction mixture is then poured into an equal volume of ice water and the organic phase is decanted. The aqueous phase is extracted twice with 300 cm³ of dichloromethane. The dichloromethane phases are combined, washed once with water, decanted, dried on magnesium sulfate and concentrated under reduced pressure. The resulting product is introduced into a silica gel column. The expected acid is entrained with ethyl acetate and then recrystallized in hexane. 25 g of 4-(5,8-methano-5,6,7,8-tetrahydro-2 naphthyl)-4-oxo butyric acid in th form of white crystals whose melting point is 135° C. are obtained.

Elemental analysis: $C_{15}H_{16}O_3$

|  | C | H | O |
|---|---|---|---|
| Calculated | 73.75 | 6.60 | 19.65 |
| Found | 73.78 | 6.66 | 19.43 |

EXAMPLE VI

Preparation of
4-(1,4-dimethoxy-5,8-methano,5,6,7,8-tetrahydro-2-naphthyl)-4-oxo butyric acid Compound of formula I wherein $A = -CH_2-_2$, $R_1, R_3 = -CH_2-$, $R_2 = R_4 = H$, $R_5 = R_6 = OCH_3$, $R', R'' = $ oxo, $R_7 = OH$ and $R_8 = H$ To a solution, stirred at 0° C., of 30 g of 1,4-dimethoxy-5,8-methano-5,6,7,8-tetrahydro naphthalene (0.154 mole) and 17 g of succinic anhydride (0.17 mole) in 280 cm³ of anhydrous 1,2-dichloroethane, there are added, over about a 1 hour period and by small portions, 23.5 g of aluminum chloride. At the end of the addition, the mixture is stirred for 3 hours at ambient temperature and then poured into 500 cm³ of ice water. The 1,2-dichloroethane phase is decanted and the aqueous phase is extracted twice with 250 cm³ of 1,2-dichloroethane. The organic phases are combined, dried on magnesium sulfate and concentrated. 30 g of crude product are obtained which product is then recrystallized in isopropyl ether. 16 g of the magnesium sulfate acid are recovered and concentrated. 30 g of crude product which is 4-(1,4-dimethoxy-5,8-methano-5,6,7,8-tetrahydro-2-naphthyl)-4-oxo butyric acid in the form of white crystals whose melting point is 132° C. are obtained.

Elemental analysis: $C_{17}H_{20}O_5$

|  | C | H | O |
|---|---|---|---|
| Calculated | 67.09 | 6.62 | 26.29 |
| Found | 66.74 | 6.53 | 25.88 |

EXAMPLE VII

Preparation of ethyl 4-(1,1,2,3,3-pentamethyl-5-indanyl)-4-oxo butyrate

Compound of formula I wherein

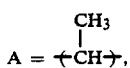

$R_1=R_2=R_3=R_4=CH_3, R_5=R_6=H$, $R',R''=oxo$, $R_7=-OC_2H_5$ and $R_8=H$

A solution of 2 g (7 mmoles) of 4-(1,1,2,3,3-pentamethyl-5-indanyl)-4-oxo butyric acid, described in Example IV, in 100 cm$^3$ of absolute ethyl alcohol containing 0.2 cm$^3$ of 98% sulfuric acid is heated for 4 hours at reflux. The solution is then concentrated under reduced pressure. The crude ester is dissolved in 100 cm$^3$ of dichloromethane and the solution is washed initially with sodium bicarbonate and then with water and finally dried on sodium sulfate. After evaporation to dryness and after drying, 1.9 g of ethyl 4-(1,1,2,3,3-pentamethyl 5-indanyl)-4-oxo butyrate in the form of a colorless liquid are obtained.

The NMR$^1$H 80 MHz spectrum conforms to the expected structure.

Elemental analysis: $C_{20}H_{28}O_3$

|  | C | H | O |
|---|---|---|---|
| Calculated | 75.91 | 8.92 | 15.17 |
| Found | 75.98 | 8.92 | 15.28 |

EXAMPLE VIII

Preparation of 2'-ethylhexyl 4-(5,5,8,8-tetramethyl-5,6,7,8-tetrahydro-2-naphthyl)-4-oxo butyrate Compound of formula I wherein $A=-CH_2-_2$, $R_1=R_2=R_3=R_4=CH_3$, $R_5=R_6=H$, $R',R''=oxo$, $R_7=-OC_8H_{17}$ and $R_8=H$ A solution of 2.88 g (10 mmoles) of 4-(5,5,8,8-tetramethyl-5,6,7,8-tetrahydro-2-naphthyl)-4-oxo butyric acid, described in Example III, in 120 cm$^3$ of toluene containing 2 g (20 mmoles) of 2-ethyl-1-hexanol and 0.1 cm$^3$ of 98% sulfuric acid is heated at reflux for 4 hours with azeotropic distillation of the water formed. The solution is then cooled, transferred into a separating funnel, thoroughly washed with water, dried on sodium sulfate and concentrated under reduced pressure. The residue is rapidly purified by passage through a silica 60 gel filter, using a 60/40 dichloromethane/toluene eluant mixture. After evaporation under a vacuum and prolonged drying, 3.6 g of 2'-ethylhexyl 4-(5,5,8,8-tetramethyl-5,6,7,8-tetrahydro-2-naphthyl)-4-oxo butyrate in the form of a colorless liquid are obtained.

The NMR$^1$H 80 MHz spectrum corresponds to the expected structure.

Elemental analysis: $C_{26}H_{40}O_3$

|  | C | H | O |
|---|---|---|---|
| Calculated | 77.95 | 10.07 | 11.98 |
| Found | 78.13 | 9.97 | 11.79 |

EXAMPLE IX

Preparation of ethyl 4-(5,5,8,8-tetramethyl-5,6,7,8-tetrahydro-2-naphthyl)-4-oxo butyrate Compound of formula I wherein $A=-CH_2-_2$, $R_1=R_2=R_3=R_4=CH_3, R_5=R_6=H$, $R',R''=oxo$, $R_7=OC_2H_5$ and $R_8=H$ A solution of 1.01 g (3.5 mmoles) of 4-(5,5,8,8-tetramethyl-5,6,7,8-tetrahydro-2-naphthyl)-4-oxo butyric acid, described in Example III, in 40 cm$^3$ of ethyl alcohol containing 0.06 cm$^3$ of 98% sulfuric acid is heated for 5 hours at reflux and then concentrated under reduced pressure. The crude ester is dissolved in 50 cm$^3$ of dichloromethane. The solution is washed initially with sodium bicarbonate and then with water, dried on sodium sulfate and evaporated to dryness. After drying, 0.9 g of ethyl 4-(5,5,8,8-tetramethyl-5,6,7,8-tetrahydro-2-naphthyl)-4-oxo butyrate in the form of a thick colorless liquid is obtained.

The NMR$^1$H 80 MHz spectrum conforms to the expected structure.

Elemental analysis: $C_{20}H_{28}O_3$

|  | C | H | O |
|---|---|---|---|
| Calculated | 75.91 | 8.92 | 15.17 |
| Found | 75.88 | 8.87 | 15.23 |

EXAMPLE X

Preparation of N-ethyl 4-(5,5,8,8-tetramethyl-5,6,7,8-tetrahydro-2-naphthyl)-4-oxo-2-methyl butyramide Compound of formula I wherein $A=-CH_2-_2$, $R_1=R_2=R_3=R_4=CH_3, R_5=R_6=H$, $R',R''=oxo$, $R_7=NHEt$ and $R_8=CH_3$ To a suspension of 3 g (10 mmoles) of 4-(5,5,8,8-tetramethyl-5,6,7,8-tetrahydro-2-naphthyl)-4-oxo-2-methyl butyric acid in 60 cm$^3$ of anhydrous dichloromethane, there are added 1.95 g (12 mmoles) of N,N'-carbonyl diimidazole. The reaction mixture is stirred for 1½ hours at ambient temperature and the resulting solution is cooled to +5° C. 0.86 cm$^3$ (13 mmoles) of anhydrous ethylamine is added and the reaction mixture is stirred for 3 hours while permitting it to return to ambient temperature. The reaction mixture is then transferred to a separatory funnel and washed initially with 0.1N HCl and then with water. The dichloromethane phase is dried on sodium sulfate and concentrated under reduced pressure. The resulting crude oil is purified by chromatography on silica 60 gel in a 5/3/2 toluene/dichloromethane/ethyl acetate mixture. After evaporation and drying 0.6 g of N-ethyl-4-(5,5,8,8-tetramethyl-5,6,7,8-tetrahydro-2-naphthyl)-4-oxo-2-methyl butyramide in the form of a white solid whose melting point is 101° C. is recovered.

The IR and NMR$^1$H 250 MHz spectra conform to the expected structure.

Elemental analysis: $C_{21}H_{31}NO_2$

|  | C | H | N | O |
|---|---|---|---|---|
| Calculated | 76.55 | 9.48 | 4.25 | 9.71 |
| Found | 76.53 | 9.54 | 4.16 | 9.84 |

EXAMPLE XI

Preparation of 4'N-(2-hydroxyethyl) piperazinyl 4-(5,5,8,8-tetramethyl-5,6,7,8-tetrahydro-2-naphthyl)-4-oxo butyramide Compound of formula I wherein $A=-CH_2-_2$, $R_1=R_2=R_3=R_4=CH_3$, $R_5=R_6=H$, $R',R''=oxo$,

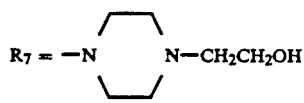

and $R_8=H$

A suspension of 2.88 g (10 mmoles) of 4-(5,5,8,8-tetramethyl-5,6,7,8-tetrahydro-2-naphthyl)-4-oxo butyric acid and 1.95 g (12 mmoles) of N,N'-carbonyl diimidazole in 50 cm³ of anhydrous dichloromethane is stirred for 1¼ hours at ambient temperature. The resulting solution is then cooled to +5° C. and 1.47 cm³ (12 mmoles) of N-2-hydroxyethyl piperazine are added. Stirring is continued for 2 hours while permitting the reaction mixture to return to ambient temperature. The reaction mixture is then transferred to a separatory funnel and copiously washed with water. The dichloromethane phase is dried on sodium sulfate and concentrated under reduced pressure. The resulting crude solid is purified by chromatography on silica 60 gel in tetrahydrofuran. After evaporation and drying 1.7 g of N-4'-(2-hydroxyethyl) piperazinyl 4-(5,5,8,8-tetramethyl-5,6,7,8-tetrahydro-2-naphthyl)-4-oxo butyramide in the form of a white powder whose melting point is 115° C. are recovered.

The NMR¹H 250 MHz spectrum conforms to the expected structure.

Elemental analysis: $C_{22}H_{36}N_2O_3$

|  | C | H | N | O |
|---|---|---|---|---|
| Calculated | 71.96 | 9.06 | 7.00 | 11.98 |
| Found | 72.01 | 9.11 | 7.04 | 12.03 |

EXAMPLE XII

Preparation of N-(2-hydroxyethoxyethyl) 4-(5,5,8,8-tetramethyl-5,6,7,8-tetrahydro-2-naphthyl)-4-oxo butyramide Compound of formula I wherein $A=-CH_2-_2$, $R_1=R_2=R_3=R_4=CH_3$, $R_5=R_6=H$, $R', R''=oxo$, $R_7=-NH-(CH_2-_2O-(CH_2-_2OH$ and $R_8=H$ A suspension of 2.88 g (10 mmoles) of 4-(5,5,8,8-tetramethyl-5,6,7,8-tetrahydro-2-naphthyl)-4-oxo butyric acid, described in Example III, and 1.95 g (12 mmoles) of N,N'-carbonyl diimidazole in 50 cm³ of anhydrous dichloromethane is stirred for 2 hours at ambient temperature. The resulting solution is cooled to a temperature between +5° and +10° C. and 1.26 g (12 mmoles) of N-2-hydroxyethoxyethylamine are added. Stirring is continued for 3 hours while permitting the reaction mixture to return to ambient temperature. The reaction mixture is transferred to a separatory funnel and diluted to 100 cm³. After washing with 0.1N HCl and then with water, the dichloromethane phase is dried on sodium sulfate and then evaporated to dryness. The residue is purified by chromatography on silica 60 gel in a 40/25/25/10 dichloromethane/toluene/ethyl acetate/isopropanol eluant mixture. After evaporation and drying, there are obtained 2.5 g of N-(2-hydroxyethoxyethyl) 4-(5,5,8,8-tetramethyl-5,6,7,8-tetrahydro-2-naphthyl)-4-oxo butyramide in the form of a thick colorless oil kept out of contact with light.

The NMR¹H 250 MHz spectrum conforms to the expected structure.

Elemental analysis: $C_{22}H_{33}NO_4 \cdot 0.5H_2O$

|  | C | H | N | O |
|---|---|---|---|---|
| Calculated | 68.72 | 8.91 | 3.64 | 18.72 |
| Found | 68.70 | 8.95 | 3.65 | 18.66 |

EXAMPLE XIII

Preparation of 4-(5,5,8,8-tetramethyl-5,6,7,8-tetrahydro-2-naphtyl)-4-hydroxy butyric acid Compound of formula I wherein $A=-CH_2-_2$, $R_1=R_2=R_3=R_4=CH_3, R_5=R_6=H$, $R'=OH$, $R''=H$, $R_7=OH$ and $R_8=H$ To a solution of 2.02 g (7 mmoles) of 4-(5,5,8,8-tetramethyl-5,6,7,8-tetrahydro-2-naphthyl)-4-oxo butyric acid described in Example III, in 60 cm³ of anhydrous tetrahydrofuran there are added 1.06 g (21 mmoles) of sodium borohydride. The reaction mixture is stirred overnight at ambient temperature. It is then cooled to about 10° C. and acidified by the slow addition of 0.1N HCl. The mixture is extracted with ethyl ether (3×100 cm³). The organic phase is washed with water, dried on sodium sulfate and evaporated to dryness. The resulting solid is taken up in 100 cm³ of hexane and filtered. 1.75 g of the expected product in admixture with its lactone are obtained. 20 cm³ of 0.5N soda are added and the reaction mixture is heated for 1 hour at reflux. The solution is then cooled to ambient temperature and acidified by the addition of 0.6 cm³ of glacial acetic acid. The resulting precipitate is filtered, washed abundantly with water and dried under a vacuum at 50° C. 1.7 g of 4-(5,5,8,8-tetramethyl-5,6,7,8-tetrahydro-2-naphthyl)-4-hydroxy butyric acid in the form of a white solid whose melting point is 110° C. are obtained.

The IR and NMR¹H 80 MHz spectra conform to the expected structure.

Elemental analysis: $C_{18}H_{26}O_3$

|  | C | H | O |
|---|---|---|---|
| Calculated | 74.44 | 9.02 | 16.53 |
| Found | 74.85 | 8.78 | 16.42 |

EXAMPLE XIV

Preparation of ethyl 4-(5,5,8,8-tetramethyl-5,6,7,8-tetrahydro-2-naphthyl)-4-hydroxyimino butyrate Compound of formula I wherein $A=-CH_2-_2$, $R_1=R_2=R_3=R_4=CH_3, R_5=R_6=H$, $R'$, $R''=N-OH$, $R_7$ $OC_2H_5$ and $R_8=H$ To a solution of 9.96 g (0.0315 mole) of ethyl 4-(5,5,8,8-tetramethyl-5,6,7,8-tetrahydro-2-naphthyl)-4-oxo butyrate, described in Example IX, in 250 cm³ of ethyl alcohol, there are added initially 4.38 g (0.063 mole) of hydroxylamine hydrochloride and then 8.9 cm³ (0.063 mole) of triethylamine. The reaction mixture is heated for 12 hours at reflux. After concentration under reduced pressure, the residue is taken up in 200 cm³ of dichloromethane. The solution is washed first with dilute HCl and then with water. The dichloromethane phase is dried on sodium sulfate and evaporated to dryness. The crude product is then purified by chromatography on silica 60 gel in a 6/3/1 toluene/dichloromethane/tetrahydrofuran mixture. After evaporation and drying, 6.6 g of ethyl 4-(5,5,8,8-tetramethyl-5,6,7,8-tetrahydro-2-naphthyl)-4-hydroxyimino butyrate in the form of a colorless liquid are recovered.

The NMR¹H 80 MHz spectrum conforms to the expected structure.

Elemental analysis: $C_{20}H_{29}NO_3$

|  | C | H | N | O |
|---|---|---|---|---|
| Calculated | 72.47 | 8.82 | 4.23 | 14.48 |
| Found | 72.46 | 8.90 | 4.15 | 14.43 |

EXAMPLE XV

Preparation of 4-(5,5,8,8-tetramethyl-5,6,7,8-tetrahydro-2-naphthyl)-4-hydroxyimino butyric acid Compound of formula I wherein $A=-CH_2-_2$, $R_1=R_2=R_3=R_4=CH_3, R_5=R_6=H$, $R',R''=N-OH$, $R_7=OH$ and $R_8=H$ A solution of 2 g (6 mmoles) of ethyl 4-(5,5,8,8-tetramethyl-5,6,7,8-tetrahydro-2-naphthyl)-4-hydrdroxyimino butyrate, described in Example XIV, in a mixture of 30 cm³ of ethyl alcohol and 30 cm³ of 2N potash is heated for 2 hours at 60° C. After cooling to ambient temperature, 100 cm³ of water are added and the alcohol is evaporated under reduced pressure. The acid is precipitated by the addition of 12N HCl. After filtration, washing with water and drying, the crude product is recrystallized in isopropyl ether. 1.4 g of white crystals of 4-(5,5,8,8-tetramethyl-5,6,7,8-tetrahydro-2-naphthyl)-4-hydroxyimino butyric acid whose melting point is 146° C. are obtained.

The NMR¹H 250 MHz spectrum conforms to the expected structure.

Elemental analysis: $C_{18}H_{25}NO_3$

|  | C | H | N | O |
|---|---|---|---|---|
| Calculated | 71.26 | 8.31 | 4.62 | 15.82 |
| Found | 71.37 | 8.29 | 4.62 | 16.04 |

EXAMPLE XVI

Preparation of 4-(5,5,8,8-tetramethyl 5,6,7,8-tetrahydro-2-naphthyl) butyric acid Compound of formula I where $A=-CH_2-_2$, $R_1=R_2=R_3=R_4=CH_3, R_5=R_6=H, R'=R''=H$, $R_7=OH$ and $R_8=H$ To a mixture of 6 g zinc wool and 0.6 g of mercuric chloride, there are added 9 cm³ of water and 0.3 cm³ of 12N HCl. The mixture is stirred for 10 minutes at ambient temperature. The aqueous phase is removed by decanting. The resulting amalgam is rinsed with 20 cm³ of water. There are added 7.21 g (0.025 mole) of 4-(5,5,8,8-tetramethyl-5,6,7,8-tetrahydro-2-naphthyl)-4-oxo butyric acid, described in Example III, 10 cm³ of water, 8 cm³ of toluene and 5 cm³ of 12N HCl. The mixture is heated for 34 hours at reflux with stirring, adding 3 cm³ of 12N HCl every 6 hours. The reaction mixture is diluted by the addition of 100 cm³ of toluene, filtered (separation of residual amalgam) and rinsed with toluene. The toluene phase is separated, washed copiously with water, dried on sodium sulfate and concentrated under reduced pressure. The resulting crude oil is purified by chromatography on silica 60 gel in a 2/8/90 acetic acid/dioxan/toluene eluant mixture. After evaporation, the recovered solid is taken up in a minimum of isopropyl ether, filtered and dried under a vacuum at 70° C. 4.6 g of 4-(5,5,8,8-tetramethyl-5,6,7,8-tetrahydro-2-naphthyl) butyric acid in the form of a white solid whose melting point is 99° C. are obtained.

The NMR¹H 80 MHz spectrum conforms to the expected structure.

Elemental analysis: $C_{18}H_{26}O_2$

|  | C | H | O |
|---|---|---|---|
| Calculated | 78.79 | 9.55 | 11.66 |
| Found | 78.73 | 9.53 | 11.44 |

EXAMPLE XVII

Preparation of sodium 4-(5,5,8,8,-tetramethyl-5,6,7,8-tetrahydro-2-naphthyl)-4-oxo-2-methyl butyrate Compound of formula I wherein $A=-CH_2-_2$, $R_1=R_2=R_3=R_4=CH_3, R_5=R_6=H, R'=R''=$oxo, $R_7=-O-Na^+$ and $R_8=CH_3$ 1.028 g (3.39 mmoles) of 4-(5,5,8,8-tetramethyl-5,6,7,8-tetrahydro-2-naphthyl)-4-oxo-2-methyl butyric acid, described in Example I, are suspended in 350 cm³ of bipermuted water. 33.9 cm³ of 0.1N aqueous soda (3.39 mmoles) are added and the mixture is stirred while cooling until dissolution. The resulting solution is filtered, then evaporated to dryness under reduced pressure. After drying under a vacuum at 80° C., 1.09 g of sodium 4-(5,5,8,8-tetramethyl-5,6,7,8-tetrahydro-2-naphthyl)-4-oxo-2-methyl butyrate in the form of a white solid that becomes vitreous at about 80° C. are recovered.

EXAMPLE XVIII

Preparation of sodium 4-(5,5,8,8-tetramethyl-5,6,7,8-tetrahydro-2-naphthyl)-4-oxo butyrate Compound of formula I wherein $A= -CH_2-_2$, $R_1=R_2=R_3=R_4=CH_3$, $R_5=R_6=H$, $R',R''=oxo$, $R_7=-O^{-Na+}$ and $R_8=H$ 0.502 g (1.74 mmoles) of 4-(5,5,8,8-tetramethyl-5,6,7,8-tetrahydro-2-naphthyl)-4-oxo butyric acid, described in Example III is suspended in 200 cm³ of bipermuted water. 17.4 cm³ (1.74 mmoles) of 0.1N aqueous soda are added and the mixture is stirred, while cooling, until dissolution. The resulting solution is filtered and then evaporated to dryness. After drying under a vaccuum at 80° C., 0.52 g of sodium 4-(5,5,8,8-tetramethyl-5,6,7,8-tetrahydro-2-naphthyl)-4-oxo butyrate in the form of a white solid whose melting point is greater than 250° C. is recovered.

EXAMPLE XIX

Preparation of zinc 4-(5,5,8,8-tetramethyl-5,6,7,8-tetrahydro-2-naphthyl)-4-oxo-2-methyl butyrate Compound of formula I wherein $A=-CH_2-_2$, $R_1=R_2=R_3=R_4=CH_3$, $R_5=R_6=H$, $R',R''=oxo$, $R_7=-O^\ominus, \frac{1}{2}Zn^{2\oplus}$, and $R_8=CH_3$ 308 mg (0.95 mmole) of sodium 4-(5,5,8,8-tetramethyl-5,6,7,8-tetrahydro-2-naphthyl)-4-oxo-2-methyl butyrate, obtained in Example XVII, are dissolved in 150 cm³ of water. 136.5 mg (0.475 mmole) of zinc sulfate.7-H₂O are added and the zinc salt precipitates. This precipitate is filtered, washed with water and dried under a vaccum at 70°-80° C. 0.32 g of zinc 4-(5,5,8,8-tetramethyl-5,6,7,8-tetrahydro-2-naphthyl)-4-oxo-2-methyl butyrate in the form of a white solid that becomes vitreous at about 115° C. is obtained.

EXAMPLE XX

Preparation of zinc 4-(5,5,8,8-tetramethyl-5,6,7,8-tetrahydro-2-naphthyl)-4-oxo butyrate Compound of formula I wherein $A=-CH_2-_2$, $R_1=R_2=R_3=R_4=CH_3$, $R_5=R_6=H$, $R',R''=oxo$, $R_7=-O^\ominus, \frac{1}{2}Zn^{2\oplus}$ and $R_8=H$ 317 mg (1.02 mmoles) of sodium 4-(5,5,8,8-tetramethyl-5,6,7,8-tetrahydro-2-naphthyl)-4-oxobutyrate, obtained in Example XVIII are dissolved in 150 cm³ of water. 147 mg (0.51 mmole) of zinc sulfate .7H₂O are added and the resulting precipitate is filtered, washed with water and dried under a vacuum at 80° C. 0.33 g of zinc 4-(5,5,8,8-tetramethyl-5,6,7,8-tetrahydro-2-naphthyl)-4-oxo butyrate in the form of a white solid that becomes vitreous at about 125° C. is obtained.

| Examples of Compositions | |
|---|---|
| Example 1 - Anti-seborrhea lotion | |
| Absolute alcohol | 59.0 g |
| Propylene glycol | 40.0 g |
| 4-(5,5,8,8-tetramethyl-5,6,7,8-tetrahydro-2-naphthyl)-4-oxo butyric acid | 1.0 g |
| Example 2 - Lotion for combatting oily skin | |
| Absolute alcohol | 60.0 g |
| Polyethylene glycol | 39.5 g |
| 4-(5,5,8,8-tetramethyl-5,6,7,8-tetrahydro-2-naphthyl)-4-oxo-2-methyl butyric acid | 0.5 g |

| -continued | |
|---|---|
| Examples of Compositions | |
| Example 3 - Gel for combatting oily skin having acne tendencies | |
| Carbopol 941 | 0.8 g |
| Absolute alcohol | 32.15 g |
| Propylene glycol | 35.0 g |
| Butylhydroxytoluene | 0.02 g |
| Butylhydroxyanisole | 0.03 g |
| Triethanolamine, 20% | 1.0 g |
| Purified water | 30.0 g |
| 4-(5,5,8,8-tetramethyl-5,6,7,8-tetrahydro-2-naphthyl)-4-oxo butyric acid | 1.0 g |
| Example 4 - Gel for combatting oily skin having acne tendencies | |
| Klucel H (cellulose derivative) | 1.0 g |
| Absolute alcohol | 69.0 g |
| Propylene glycol | 28.45 g |
| Butylhydroxytoluene | 0.02 g |
| Butylhydroxyanisole | 0.03 g |
| N-(2-hydroxyethoxyethyl)-4-(5,5,8,8-tetramethyl-5,6,7,8-tetrahydro-2-naphthyl)-4-oxo butyramide | 1.5 g |
| Example 5 - Cream for oily skin | |
| Glycol monostearate | 4.0 g |
| Cetyl alcohol | 3.5 g |
| Polyethylene glycol stearate (50 moles of ethylene oxide) sold under the trade name "Myrj 53" by Atlas | 3.0 g |
| Capric/caprylic triglycerides | 22.0 g |
| Propyl parahydroxybenzoate | 0.15 g |
| Butylhydroxytoluene | 0.02 g |
| Butylhydroxyanisole | 0.03 g |
| Propyleneglycol | 8.0 g |
| 2'-ethylhexyl-4-(5,5,8,8-tetramethyl-5,6,7,8-tetrahydro-2-naphthyl)-4-oxo butyrate | 2.0 g |
| Water, sufficient amount for | 100.0 g |
| Example 6 - Stick (coloring) for oily skin | |
| Petrolatum | 19.4 g |
| Perhydrosqualene - Cosbiol | 40.0 g |
| Solid paraffin | 2.0 g |
| Carnauba wax | 2.0 g |
| Ozokerite | 9.0 g |
| Butylhydroxyanisole | 0.05 g |
| Butylhydroxytoluene | 0.05 g |
| Red iron oxide | 0.5 g |
| Yellow iron oxide | 1.5 g |
| Brown iron oxide | 2.5 g |
| Titanium oxide | 20.0 g |
| 4-(5,5,8,8-tetramethyl-5,6,7,8-tetrahydro-2-naphthyl)-4-hydroxy butyric acid | 1.0 g |
| Rice starch | 2.0 g |

What is claimed is:

1. Aromatic derivative of butyric acid having the formula

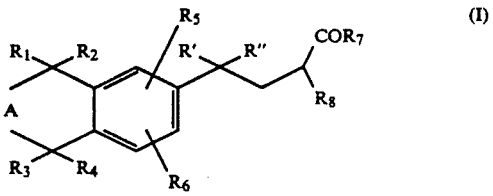

wherein $R_1$, $R_2$, $R_3$ and $R_4$, each independently, represent hydrogen or lower alkyl, with at least two of $R_1$–$R_4$ being other than hydrogen, A represents methylene or dimethylene, substituted or not by lower alkyl;

$R_5$ and $R_6$ represent hydrogen, halogen, lower alkyl, lower alkoxy and hydroxy, R' and R" taken together form oxo,
R8 represents hydrogen or lower alkyl,
R7 represents —OR9 or

R9 represents hydrogen, alkyl having 1–20 carbon atoms, monohydroxyalkyl, polyhydroxyalkyl, aryl or aralkyl, optionally substituted, carboxyalkyl or alkoxycarbonylalkyl, r' and r" represent hydrogen, lower alkyl, monohydroxyalkyl optionally interrupted by a heteroatom, polyhydroxyalkyl, or aryl or benzyl optionally substituted, or r' and r" taken together form a heterocycle optionally substituted by $C_1$–$C_3$ hydroxyalkyl, or the salts of the aromatic derivative of formula I and its optical isomers as well as the tautomer forms of the aromatic derivative of formula I.

2. The aromatic derivative of claim 1 wherein said lower alkyl or alkyl having 1–20 carbon atoms is selected from the group consisting of methyl, ethyl, propyl, isopropyl, butyl, tert.butyl, 2-ethylhexyl, octyl, dodecyl, hexadecyl and octadecyl.

3. The aromatic derivative of claim 1 wherein said monohydroxyalkyl is 2-hydroxy ethyl, 2-hydroxy propyl or 2-hydroxyethoxyethyl.

4. The aromatic derivative of claim 1 wherein said polyhydroxyalkyl is 2,3-dihydroxy propyl, 1,3-dihydroxypropyl or the residue of pentaerythritol.

5. The aromatic derivative of claim 1 wherein said lower alkoxy is methoxy, isopropoxy, butoxy or tert. butoxy.

6. The aromatic derivative of claim 1 wherein r' and r", taken together, form with the nitrogen atom to which they are attached, piperidino, piperazino, morpholino, pyrrolidino or 4-(2-hydroxyethyl) piperazino.

7. The aromatic derivative of claim 1 having the formula

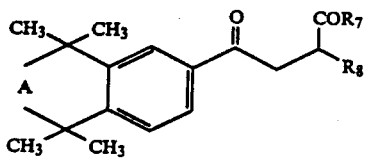

wherein
A represents —$CH_2$—2 or

R7 represents —OR9 or

R9 represents hydrogen or lower alkyl,
r' represents hydrogen and r" represents alkyl having 1–8 carbon atoms, monohydroxyalkyl optionally interrupted by a heteroatom or polyhydroxyalkyl or r' and r", taken together, form with the nitrogen atom to which they are attached, 4-(2-hydroxyethyl) piperazinyl, and R8 represents hydrogen or methyl.

8. A process for preparing the aromatic derivative of butyric acid of claim 1 comprising reacting, under Friedel-Crafts reaction conditions, an acid anhydride of formula (2)

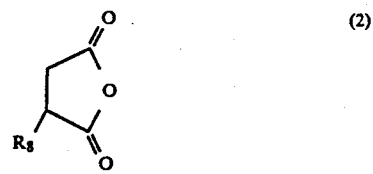

with a bicyclic aromatic compound of formula (1)

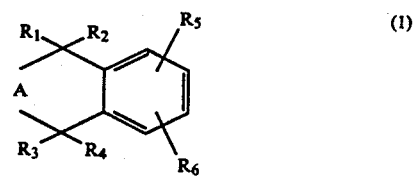

wherein A, $R_1$ to $R_6$ and $R_8$ have the meanings given in claim 1 and, if required, subjecting the resulting keto-acid to conventional reactions to produce the remaining aromatic derivatives of forumla I.

9. The process of claim 8 wherein the reaction of said acid anhydride with said bicyclic aromatic compound is carried out in the presence of a Lewis acid in a chlorinated solvent.

10. The process of claim 9 wherein said Lewis acid is aluminum chloride or tin chloride.

11. The process of claim 8 wherein the said keto-acid is reduced to the corresponding hydroxy acid in the presence of sodium borohydride in tetrahydrofuran or in the presence of zinc in an alkaline medium.

12. The process of claim 8 wherein the ketone function of said keto-acid is reduced with a zinc amalgam in the presence of hydrochloric acid.

13. A cosmetic composition comprising in a cosmetically acceptable medium at least one aromatic derivative of claim 1.

14. The cosmetic composition of claim 13 wherein said aromatic derivative is present in an amount ranging from 0.005 to 5 percent by weight based on the total weight of said composition.

15. The cosmetic composition of claim 13 wherein said aromatic derivative is present in an amount ranging from 0.01 to 1 percent by weight based on the total weight of said composition.

16. A pharmaceutical composition comprising in a pharmaceutically acceptable carrier and for enteral, parenteral or topical application, at least one aromatic derivative of claim 1.

17. The pharmaceutical composition of claim 16 in a form for topical application wherein said aromatic derivative is present in an amount ranging from 0.01 to 10 percent by weight based on the total weight of said composition.

18. The pharmaceutical composition of claim 17 wherein said aromatic derivative is present in an amount ranging from 0.1 to 5 percent by weight based on the total weight of said composition.

19. A composition comprising in a cosmetically or pharmaceutically acceptable vehicle at least one aromatic derivative of claim 1 and at least one of a hydrating agent, an anti-seborrhea agent, an anti-acne agent, an anti-biotic, an agent for promoting hair growth, an anti-inflammatory agent, a carotinoid or an anti-psoriasis agent.

20. The aromatic derivative of claim 1 or a salt or isomer thereof, selected from the group consisting of
4-(5,5,8,8-tetramethyl-5,6,7,8-tetrahydro-2-naphthyl)-4-oxo-2-methyl butyric acid,
4-(1,1,2,3,3-pentamethyl-5-indanyl)-4-oxo-2-methyl butyric acid,
4-(1,1,3,3-tetramethyl-5-indanyl)-4-oxo-2-methyl butyric acid,
4-(5,5,8,8-tetramethyl-5,6,7,8-tetrahydro-2-naphthyl)-4-oxo-butyric acid,
4-(1,1,2,3,3-pentamethyl-5-indanyl)-4-oxo butyric acid,
4-(1,1,3,3-tetramethyl-5-indanyl)-4-oxo butyric acid,
ethyl 4-(1,1,2,3,3-pentamethyl-5-indanyl)-4-oxo butyric acid,
ethyl 4-(5,5,8,8-tetramethyl-5,6,7,8-tetrahydro-2-naphthyl)-4-oxo butyrate,
2'-ethylhexyl 4-(5,5,8,8-tetramethyl -5,6,7,8-tetrahydro-2-naphthyl)-4-oxo butyrate,
N-ethyl 4-(5,5,8,8-tetramethyl-5,6,7,8-tetrahydro-2-naphthyl)-4-oxo butyramide,
N-ethyl 4-(5,5,8,8-tetramethyl-5,6,7,8-tetrahydro-2-naphthyl)-4oxo butyramide,
4'-N-(2-hydroxyethyl) piperazinyl 4-(5,5,8,8-tetramethyl-5,6,7,8-tetrahydro-2-naphthyl)-4-oxo butyramide,
N-(2-hydroxyethoxyethyl) 4-(5,5,8,8-tetramethyl-5,6,7,8-tetrahydro-2-naphthyl)-4-oxo butyramide,
N-(2-hydroxyethoxyethyl) 4-(1,1,2,3,3-pentamethyl-5-indanyl)-4-oxo butyramide,
sodium 4-(5,5,8,8-tetramethyl-5,6,7,8-tetrahydro-2-naphthyl)-4-oxo butyrate,
sodium 4-(5,5,8,8-tetramethyl-5,6,7,8-tetrahydro-2-naphthyl)-4-oxo-2-methyl butyrate,
zinc 4-(5,5,8,8-tetramethyl-5,6,7,8-tetrahydro-2-naphthyl)-4-oxo butyrate,
zinc 4-(1,1,2,3,3-pentamethyl-5-indanyl) oxo butyrate and
zinc 4-(5,5,8,8-tetramethyl-5,6,7,8-tetrahydro-2-naphthyl)-4-oxo-2-methyl butyrate.

21. The aromatic derivative of claim 1 which is 4-(5,5,8,8-tetramethyl-5,6,7,8-tetrahydro-2-naphthyl)-4-oxo butyric acid.

* * * * *